United States Patent
Bjørnvad et al.

(10) Patent No.: US 6,207,436 B1
(45) Date of Patent: Mar. 27, 2001

(54) ENDO-B-1,4-GLUCANASES FROM SACCHAROTHRIX

(75) Inventors: Mads Eskelund Bjørnvad, Frederiksberg (DK); Mariko Hatakeyama, Fairfield, CA (US); Martin Schülein, Copenhagen; Jack Bech Nielsen, Hellerup, both of (DK)

(73) Assignee: NovoNordisk A/S, Bagsvaerd (DK)

( * ) Notice: Subject to any disclaimer, the term of this patent is extended or adjusted under 35 U.S.C. 154(b) by 0 days.

(21) Appl. No.: 09/109,841

(22) Filed: Jul. 2, 1998

Related U.S. Application Data

(60) Provisional application No. 60/053,506, filed on Jul. 23, 1997.

(30) Foreign Application Priority Data

Jul. 4, 1997 (DK) .................................................. 0812/97
Jul. 11, 1997 (DK) .................................................. 0846/97

(51) Int. Cl.$^7$ ................................ C12N 9/00; C12N 9/14; C12N 9/24; C12N 9/42; C07H 21/04
(52) U.S. Cl. ........................ 435/209; 435/183; 435/195; 435/200; 536/23.2
(58) Field of Search ................................... 435/183, 203, 435/209, 210, 211, 252.33; 536/23.2

(56) References Cited

U.S. PATENT DOCUMENTS 5,643,791 7/1997 Warren et al. .

FOREIGN PATENT DOCUMENTS

WO 89/09259 10/1989 (WO) .

OTHER PUBLICATIONS

`Ethier et al. (1994) Canadian Journal of Microbiol. 40 (5) :361–368.
Ghangas et al. (1988) Applied And Environ. Microbiol. 54(10) :2521–2526.
Henrissat et al. (1993) Biochem. J. 293:781–788.
Maidak et al. (1996) Nucleic Acids Research 24(1):82–85.
Gilbert et al. (1993) J. of General Microbiology 139:187–194.
Raymond Wong et al. Characterization and structure of an endoglucanase gene cenA of Cellulomonas fimi. Gene vol. 44:315–324. 1986.*

* cited by examiner

*Primary Examiner*—Rebecca E. Prouty
*Assistant Examiner*—Manjunath N. Rao
(74) *Attorney, Agent, or Firm*—Elisa J. Laubiris, Esq.

(57) ABSTRACT

An enzyme preparation comprising an enzyme having endo-β-1,4-glucanase activity obtainable from or endogeneous to a strain belonging to the genus Saccharothrix such as *Saccharothrix australiensis*, IFO 14444; an isolated polynucleotide (DNA) molecule encoding an enzyme or enzyme core (the catalytically active domain of the enzyme) exhibiting endo-β-1,4-glucanase activity selected from (a) polynucleotide molecules comprising a nucleotide sequence as shown in SEQ ID NO:1 from nucleotide 676 to nucleotide 1470, (b) polynucleotide molecules that encode a polypeptide that is at least 80% identical to the amino acid sequence of SEQ ID NO:2 from amino acid residue 226 to amino acid residue 490, and (c) degenerate nucleotide sequences of (a) or (b), the expressed endoglucanase and the enzyme preparation being useful in a detergent or fabric softener composition or in the textile industry for improving the properties of cellulosic fibres or fabric or for providing a stone-washed look of denim.

6 Claims, No Drawings and 0812/97, filed Jul. 4, 1997, and U.S. provisional application Ser. No. 60/053,506, filed Jul. 23, 1997, the contents of which are fully incorporated herein by reference.

SEQUENCE LISTING

<160> NUMBER OF SEQ ID NOS: 4

<210> SEQ ID NO 1
<211> LENGTH: 1470
<212> TYPE: DNA
<213> ORGANISM: Saccharothrix australiensis -continued

```
<400> SEQUENCE: 1
atgcaccccc gctcgaagag acccctcacc accagacgca aggtcgtccc ggccgtcgcg      60
gccggaaccg tcctcgccgg cggcgtcacc gccctgacct ccaacatcgc gcaggccgcc     120
gccggctgcc gcgtcgacta cgccgtgacg agccagtggc ccggtggctt cggtgcagcc     180
gtcaccgtca cgaacctcgg cgacccgctc tcgtcctggg agctgagctg gacgttcccc     240
gacggccagg gcgtgcagca gctctggaac ggcgtgcact cgacctccgg ttcgaacgtc     300
accgtgaaag aaatgtcgtg gaacggttcg gtcggcacca cgccagcgt ccaggtcggc     360 ttcaacggct cctggaacgg cgcgaacaac gcgccgacgt ccttcacgct caacggcacc     420
tcgtgcaacg gtgcggtcgg tggcccgacg acggagccga cgcccgagcc gaccccggag     480
cccacgcccg agccgacgcc ggagccgacg cccgagccga cgccggagcc cacgcccgag     540
ccgacgccgg agcccacgcc cgagccgacc cggagcccca cgcccgagcc cacgcccgag     600
cccacgcccg agcccacgat gccgccggtc caggccggtc agttccacgt cgacaccacg     660
aaccagtcgt accgcgcctg gcaggcggcc agcggctccg acaaggacct gctggcgaag     720
atcgccctga cgccgcaggc gtactgggtc ggcaactgga acgaagcctc gcacgcgcag     780
caggaagtcc gtgacatcac gtcggccgct gcggccgccg gcaggaccgc cgtgctcgtc     840
gtctacgcca tcccgggccg cgactgcggc cagcactcca gcggcggcgt gtcgacctcc     900
gagtacgcgc agtggatcga cacggtcgcc cagggcatcg tcggcaaccc gtgggtggtc     960
ctcgaccccg acgcgctgcc gatgctcggc gactgcgacg gccagggcga ccgggtcggc    1020
ttcctcaagt acgccgcgaa gtccctgacc gccaagggtg cgcgcgtcta catcgacgcc    1080
ggccactcgg cgtggctgtc gccgtcggaa gccgcgaacc gcctcaacca gatcgggttc    1140
gaggacgccg tgggcttctc gatcaacgtc tccaactacc gcacgacggc ggagtcgaag    1200
acctggggtc agcaggtctc gcagctgacc ggtggcaaga agttcgtcat cgacacgtcg    1260
cgcaacggca acggcccgtc cgggtcggaa tggtgcaacc cgagcggccg cgccctcggc    1320
gagcgcccga cgctcgtgaa cgaccgcagc gggctcgacg cgctgctgtg gatcaagctg    1380
cccggtgagt cggacggcgc ctgcaacggc ggcccgggcg ccggtcagtg gtggcactcc    1440
atggcactgg ctggccgcaa cgcgaagtgg                                     1470

<210> SEQ ID NO 2
<211> LENGTH: 490
<212> TYPE: PRT
<213> ORGANISM: Saccharothrix australiensis

<400> SEQUENCE: 2

Met His Pro Arg Ser Lys Arg Pro Leu Thr Thr Arg Arg Lys Val Val
  1               5                  10                  15

Pro Ala Val Ala Ala Gly Thr Val Leu Ala Gly Val Thr Ala Leu
                 20                  25                  30

Thr Ser Asn Ile Ala Gln Ala Ala Gly Cys Arg Val Asp Tyr Ala
             35                  40                  45

Val Thr Ser Gln Trp Pro Gly Gly Phe Gly Ala Ala Val Thr Val Thr
         50                  55                  60

Asn Leu Gly Asp Pro Leu Ser Ser Trp Glu Leu Ser Trp Thr Phe Pro
 65                  70                  75                  80

Asp Gly Gln Gly Val Gln Gln Leu Trp Asn Gly Val His Ser Thr Ser
                 85                  90                  95

Gly Ser Asn Val Thr Val Lys Glu Met Ser Trp Asn Gly Ser Val Gly
```

```
                    100                 105                 110
Thr Asn Ala Ser Val Gln Val Gly Phe Asn Gly Ser Trp Asn Gly Ala
                115                 120                 125
Asn Asn Ala Pro Thr Ser Phe Thr Leu Asn Gly Thr Ser Cys Asn Gly
                130                 135                 140
Ala Val Gly Gly Pro Thr Thr Glu Pro Thr Pro Glu Pro Thr Pro Glu
145                 150                 155                 160
Pro Thr Pro Glu Pro Thr Pro Glu Pro Thr Pro Glu Pro Thr Pro Glu
                165                 170                 175
Pro Thr Pro Glu Pro Thr Pro Glu Pro Thr Pro Glu Pro Thr Pro Glu
                180                 185                 190
Pro Thr Pro Glu Pro Thr Pro Glu Pro Thr Pro Glu Pro Thr Met Pro
                195                 200                 205
Pro Val Gln Ala Gly Gln Phe His Val Asp Thr Thr Asn Gln Ser Tyr
                210                 215                 220
Arg Ala Trp Gln Ala Ala Ser Gly Ser Asp Lys Asp Leu Leu Ala Lys
225                 230                 235                 240
Ile Ala Leu Thr Pro Gln Ala Tyr Trp Val Gly Asn Trp Asn Glu Ala
                245                 250                 255
Ser His Ala Gln Gln Glu Val Arg Asp Ile Thr Ser Ala Ala Ala Ala
                260                 265                 270
Ala Gly Arg Thr Ala Val Leu Val Tyr Ala Ile Pro Gly Arg Asp
                275                 280                 285
Cys Gly Gln His Ser Ser Gly Val Ser Thr Ser Glu Tyr Ala Gln
                290                 295                 300
Trp Ile Asp Thr Val Ala Gln Gly Ile Val Gly Asn Pro Trp Val Val
305                 310                 315                 320
Leu Asp Pro Asp Ala Leu Pro Met Leu Gly Asp Cys Asp Gly Gln Gly
                325                 330                 335
Asp Arg Val Gly Phe Leu Lys Tyr Ala Ala Lys Ser Leu Thr Ala Lys
                340                 345                 350
Gly Ala Arg Val Tyr Ile Asp Ala Gly His Ser Ala Trp Leu Ser Pro
                355                 360                 365
Ser Glu Ala Ala Asn Arg Leu Asn Gln Ile Gly Phe Glu Asp Ala Val
                370                 375                 380
Gly Phe Ser Ile Asn Val Ser Asn Tyr Arg Thr Thr Ala Glu Ser Lys
385                 390                 395                 400
Thr Trp Gly Gln Gln Val Ser Gln Leu Thr Gly Gly Lys Lys Phe Val
                405                 410                 415
Ile Asp Thr Ser Arg Asn Gly Asn Gly Pro Ser Gly Ser Glu Trp Cys
                420                 425                 430
Asn Pro Ser Gly Arg Ala Leu Gly Glu Arg Pro Thr Leu Val Asn Asp
                435                 440                 445
Arg Ser Gly Leu Asp Ala Leu Leu Trp Ile Lys Leu Pro Gly Glu Ser
                450                 455                 460
Asp Gly Ala Cys Asn Gly Gly Pro Gly Ala Gly Gln Trp Trp His Ser
465                 470                 475                 480
Met Ala Leu Ala Gly Arg Asn Ala Lys Trp
                485                 490

<210> SEQ ID NO 3
<211> LENGTH: 21
<212> TYPE: DNA
<213> ORGANISM: Saccharothrix australiensis
```

```
<400> SEQUENCE: 3
ggcttttaag ccgtctgtac g                                          21

<210> SEQ ID NO 4
<211> LENGTH: 25
<212> TYPE: DNA
<213> ORGANISM: Saccharothrix australiensis

<400> SEQUENCE: 4
ctcacgttaa gggattttgg tctgg                                      25
```

ENDO-B-1,4-GLUCANASES FROM SACCHAROTHRIX

CROSS-REFERENCE TO RELATED APPLICATIONS

This application claims priority under 35 U.S.C. 119 of Danish applications Serial nos. 0846/97, filed Jul. 11, 1997, and 0812/97, filed Jul. 4, 1997, and U.S. provisional application Ser. No. 60/053,506, filed Jul. 23, 1997, the contents of which are fully incorporated herein by reference.

The present invention relates to an endo-β-1,4-glucanase preparation derived from a Saccharothrix strain, an isolated polynucleotide molecule encoding an endo-β-1,4-glucanase, an isolated enzyme produced by recombinant techniques, and use of the preparation or the enzyme in the detergent, paper and pulp, oil drilling, oil extraction, wine and juice, food ingredients, animal feed and textile industries.

BACKGROUND OF THE INVENTION

Cellulose is a polymer of glucose linked by β-1,4-glucosidic bonds. Cellulose chains form numerous intra- and intermolecular hydrogen bonds, which result in the formation of insoluble cellulose microfibrils. Microbial hydrolysis of cellulose to glucose involves the following three major classes of cellulases: (i) endoglucanases (EC 3.2.1.4) which cleave β-1,4-glucosidic links randomly throughout cellulose molecules; (ii) cellobiohydrolases (EC 3.2.1.91) which digest cellulose from the nonreducing end, releasing cellobiose; and (iii) β-glucosidases (EC 3.2.1.21) which hydrolyse cellobiose and low-molecular-mass cellodextrins to release glucose.

Cellulases are produced by many microorganisms and are often present in multiple forms. Recognition of the economic significance of the enzymatic degradation of cellulose has promoted an extensive search for microbial cellulases which can be used industrially. As a result, the enzymatic properties and the primary structures of a large number of cellulase have been investigated. On the basis of the results of a hydrophobic cluster analysis of the amino acid sequence of the catalytic domain, these cellulases have been placed into different families of glycosyl hydrolases; fungal and bacterial glycosyl hydrolases have been grouped into 35 families (Henrissat et. al. (1991), (1993)). Most cellulases consist of a cellulose-binding domain (CBD) and a catlytic domain (CAD) separated by a linker which may be rich in proline and hydroxy amino residues. Another classification of cellulases has been established on the basis of the similarity of their CBDs (Gilkes et al. (1991)) giving five families of glycosyl hydrolases (I–V).

Cellulases are synthesized by a large number of microorganisms which include fungi, actinomycetes, myxobacteria and true bacteria but also by plants. Especially endo-β-1,4-glucanases of a wide variety of specificities have been identified. Many bacterial endoglucanases have been described (Henrissat (1993); Gilbert et al.,(1993)).

According to the NCBI Taxonomy Browser (Internet address: http://www.ncbi.nlm.nih.gov/Taxonomy/tax.html), the taxonomic family Pseudonocardiaceae belongs to the order of Actinomycetes under the class of gram-positive bacteria (Firmicutes) and covers the genera Actinokineospora, Actinopolyspora, Amycolata, Amycolatopsis, Kibdelosporangium, Pseudonocardia, Saccharomonospora, Saccharopolyspora, Saccharothrix, and Thermocrispum. According to Taxonomy of bacteria and Archaea refers to the Ribosomal Database Project (B. L. Maidak et al. (1996) *Nucleic Acids Res.* 24:82–85), the Gram-Positive Phylum, High mol % G+C Subdivision comprises Streptomyces group (e.g. *Kitasatosporia setae, Streptomyces albogriseolus, Streptomyces lividans, Streptomyces celluflavus, Streptomyces flavogriseus* and *Streptomyces griseus*), Arthrobacter group (e.g. *Cellulomonas fimi, Cellulomonas gelida, Cellulomonas flavigena* and *Cellulomonas uda*), and Sachharopolyspora group (e.g. *Thermomonospora curvata, Thermomonospora mesouviformis micromonospora inositola, Saccharothix australiensis, Saccharothrix longispora, Saccharothrix mutabilis, Amycolatopsis mediterranei* and *Nocardiopsis albus*).

A very important industrial use of cellulolytic enzymes is the use for treatment of cellulosic textile or fabric, e.g. as ingredients in detergent compositions or fabric softener compositions, for bio-polishing of new fabric (garment finishing), and for obtaining a "stone-washed" look of cellulose-containing fabric, especially denim, and several methods for such treatment have been suggested, e.g. in GB-A-1 368 599, EP-A-0 307 564 and EP-A-0 435 876, WO 91/17243, WO 91/10732, WO 91/17244, PCT/DK95/000108 and PCT/DK95/00132. Another important industrial use of cellulolytic enzymes is the use for treatment of paper pulp, e.g. for improving the drainage or for deinking of recycled paper.

There is an ever existing need for providing novel cellulase enzymes or enzyme preparations which may be used for applications where cellulase, preferably an endo-β-1,4-glucanase, activity is desirable.

The object of the present invention is to provide novel enzymes and enzyme compositions having substantial cellulolytic activity under slightly acidic to alkaline conditions and improved performance in paper pulp processing, textile treatment, laundry processes, extraction processes or in animal feed; preferably are such novel well-performing endoglucanases producible or produced by using recombinant techniques in high yields.

SUMMARY OF THE INVENTION

It has now been found that a variety of strains belonging to the genus Saccharothrix produces an enzyme having substantial cellulolytic activity, i.e. an endo-β-1,4-glucanase which is endogenous to Saccharothrix, and the inventors have succeeded in cloning and expressing a DNA sequence encoding such an enzyme.

Accordingly, in its first aspect the present invention relates to an enzyme preparation comprising an enzyme having endo-β-1,4-glucanase activity which is obtainable from or endogeneous to a strain belonging to the genus Saccharothrix, preferably belonging to a strain selected from the species *Saccharothrix australiensis, Saccharothrix texasensis, Saccharothrix waywayandensis, Saccharothrix cryophilis, Saccharothrix flava, Saccharothrix coeruleofusca, Saccharothrix longispora, Saccharothrix mutabilis* ssp. *capreolus, Saccharothrix aerocolonigenes, Saccharothrix mutabilis* ssp. *mutabilis, Saccharothrix syringae,* Saccharothrix sp., and in its second aspect the invention relates to an isolated polynucleotide molecule, preferably a DNA molecule, encoding an enzyme or enzyme core (ie the catalytically active domain of the enzyme) exhibiting endo-β-1,4-glucanase activity selected from the group consisting of (a) polynucleotide molecules comprising a nucleotide sequence as shown in SEQ ID NO:1 from nucleotide 676 to nucleotide 1470, (b) polynucleotide molecules that encode a polypeptide that is at least 80% identical to the amino acid sequence of SEQ ID NO:2 from amino acid residue 226 to amino acid residue 490, and (c) degenerate nucleotide sequences of (a) or (b); preferably a polynucleotide molecule capable of hybridizing to a denatured double-stranded DNA probe under medium stringency conditions, wherein the probe is selected from the group consisting of DNA probes comprising the sequence shown in positions 676–1470 of SEQ ID NO:1 and DNA probes comprising a subsequence of positions 676–1470 of SEQ ID NO:1 having a length of at least about 100 base pairs.

A plasmid pSJ1678 comprising a DNA sequence encoding the endoglucanase of the invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Mar. 17, 1997 under the deposition number DSM 11476.

In its third, fourth and fifth aspect the invention provides an expression vector comprising a DNA segment which is eg a polynucleotide molecule of the invention; a cell comprising the DNA segment or the expression vector; and a method of producing an enzyme exhibiting cellulolytic activity, which method comprises culturing the cell under conditions permitting the production of the enzyme, and recovering the enzyme from the culture.

In yet another aspect the invention provides an isolated enzyme exhibiting cellulolytic activity, characterized in (i) being free from homologous impurities and (ii) the enzyme is produced by the method described above.

The invention further relates to an endo-beta-1,4-glucanase being either a polypeptide produced by *Saccharothrix australiensis*, IFO 14444, or a polypeptide comprising an amino acid sequence as shown in positions 226–490 of SEQ ID NO:2, or an analogue of any of these polypeptides which is at least 75% homologous therewith, or is derived from any of these polypeptides by substitution, deletion or addition of one or several amino acids, or is immunologically reactive with a polyclonal antibody raised against any of these polypeptides in purified form.

Further, the present invention relates to the use of such an enzyme or the enzyme preparation of the invention for industrial applications such as in a detergent composition or fabric softener composition intended for domestic or industrial use in conventional laundry washing processes; in industrial cleaning processes; and in the textile industry for improving the properties of cellulosic fibres or fabric or for providing a stone-washed look of denim.

The invention also relates to an isolated substantially pure biological culture of the *Escherichia coli* strain DSM 11476 harbouring a cellulase encoding DNA sequence (the cellulose encoding part of the DNA sequence cloned into plasmid pSJ1678 present in *Escherichia coli* DSM 11476 derived from a strain of the bacterial species *Saccharothrix australiensis*, or any mutant of said *E.coli* strain.

DETAILED DESCRIPTION OF THE INVENTION

The enzyme or enzyme preparation of the invention is obtainable from or endogeneous to a strain belonging to the genus Saccharothrix, preferably from the species selected from the group consisting of *Saccharothrix australiensis, Saccharothrix texasensis, Saccharothrix waywayandensis, Saccharothrix cryophilis, Saccharothrix flava, Saccharothrix coeruleofusca, Saccharothrix longispora, Saccharothrix mutabilis* ssp. *capreolus, Saccharothrix aerocolonigenes, Saccharothrix mutabilis* ssp. *mutabilis, Saccharothrix syringae,* Saccharothrix sp. Examples of useful strains are *Saccharothrix australiensis*, IFO 14444, *Saccharothrix texasensis*, NRRL B-16134, *Saccharothrix waywayandensis,* NRRL B-16159, *Saccharothrix cryophilis,* NRRL B-16238, Saccharothrix sp., IFO 13785, *Saccharothrix flava,* ATCC 29533, *Saccharothrix coeruleofusca* (*Actinomadura coeruleofusca*), ATCC 35108 or DSM 43679, *Saccharothrix longispora* (*Actinomadura longispora*), ATCC 31109 or DSM 43749, *Saccharothrix mutabilis* ssp. *mutabilis,* ATCC 31520, *Saccharothrix aerocolonigenes,* ATCC 23870, *Saccharothrix mutabilis* ssp. *capreolus,* ATCC 23892, *Saccharothrix mutabilis,* DSM 40225 or DSM 43853, *Saccharothrix syringae,* DSM 43886.

The enzyme and the enzyme preparation of the invention is active over a broad pH range, preferably active at a pH between about 4 and about 11, preferably between about 5.5 and about 10.

In a preferred embodiment, the enzyme or the enzyme preparation of the invention belongs to family 6 of glycosyl hydrolases (Henrissat et al., op.cit.).

In the present context the term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinantly expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein/polypeptide, the term "isolated" indicates that the protein is found in a condition other than is its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention) which originate from the homologous cell where the polypeptide of the invention is originally obtained from.

The term "obtained from" as used herein in connection with a specific microbial source, means that the polynucleotide and/or polypeptide produced by the specific source, or by a cell in which a gene from the source have been inserted.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

Polynucleotides:

Within preferred embodiments of the invention an isolated polynucleotide of the invention will hybridize to similar sized regions of SEQ ID No. 1, or a sequence complementary thereto, under at least medium stringency conditions.

In particular polynucleotides of the invention will hybridize to a denatured double-stranded DNA probe comprising either the full sequence shown in positions 676–1470 of SEQ ID NO:1 or any probe comprising a subsequence of SEQ ID NO:1 having a length of at least about 100 base pairs under at least medium stringency conditions, but preferably at high stringency conditions as described in detail below. Suitable experimental conditions for determining hybridization at medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 $\mu$g/ml of denatured sonicated salmon sperm DNA (Sambrook et al. 1989), followed by hybridization in the same solution containing a concentration of long/ml of a random-primed (Feinberg, A. P. and Vogelstein, B. (1983) Anal. Biochem. 132:6–13), 32P-dCTP-labeled (specific activity higher than $1\times10^9$ cpm/$\mu$g) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

As previously noted, the isolated polynucleotides of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having endoguca-nase activity of the invention are then identified and isolated by, for example, hybridization or PCR.

The present invention further provides counterpart polypeptides and polynucleotides from different bacterial strains (orthologs or paralogs). Of particular interest are endoglucanase polypeptides from gram-positive alkalophilic strains, including species of Saccharothrix.

Species homologues of a polypeptide with endoglucanase activity of the invention can be cloned using information and compositions provided by the present invention in combination with conventional cloning techniques. For example, a DNA sequence of the present invention can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA sequence of the invention encoding an polypeptide having endoglucanase activity can then be isolated by a variety of methods, such as by probing with probes designed from the sequences disclosed in the present specification and claims or with one or more sets of degenerate probes based on the disclosed sequences. A DNA sequence of the invention can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the endoglucanase cloned from *S.australienses*, IFO 14444, expressed and purified as described in Materials and Methods and Examples 1 and 3, or by an activity test relating to a polypeptide having endoglucanase activity.

The endoglucanase encoding part of the DNA sequence cloned into plasmid pSJ1678 present in *Escherichia coli* DSM 11476 and/or an analogue DNA sequence of the invention may be cloned from a strain of the bacterial species *Saccharothrix australiensis,* preferably the strain IFO 14444, producing the enzyme with endoglucanase activity, or another or related organism as described herein.

Alternatively, the analogous sequence may be constructed on the basis of the DNA sequence obtainable from the plasmid present in *Escherichia coli* DSM 11476 (which is believed to be identical to the attached SEQ ID NO:1), e.g be a sub-sequence thereof, and/or by introduction of nucleotide substitutions which do not give rise to another amino acid sequence of the mannanase encoded by the DNA sequence, but which corresponds to the codon usage of the host organism intended for production of the enzyme, or by introduction of nucleotide substitutions which may give rise to a different amino acid sequence (i.e. a variant of the mannan degrading enzyme of the invention).

Polypeptides:

The sequence of amino acids nos. 226–490 of SEQ ID NO: 2 is a mature endoglucanase sequence of the catalytic active domain.

The present invention also provides endoglucanase polypeptides that are substantially homologous to the polypeptide of SEQ ID NO:2 and species homologs (paralogs or orthologs) thereof. The term "substantially homologous" is used herein to denote polypeptides having 75%, preferably at least 80%, more preferably at least 85%, and even more preferably at least 90%, sequence identity to the sequence shown in amino acids nos. 226–490 of SEQ ID NO:2 or their orthologs or paralogs. Such polypeptides will more preferably be at least 95% identical, and most preferably 98% or more identical to the sequence shown in amino acids nos. 226–490 of SEQ ID NO:2 or its orthologs or paralogs. Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a polypeptide of the invention having endoglucanase activity.

TABLE 1

Conservative amino acid substitutions

| | |
|---|---|
| Basic | arginine |
| | lysine |
| | histidine |
| Acidic | glutamic acid |
| | aspartic acid |
| Polar | glutamine |
| | asparagine |
| Hydrophobic | leucine |
| | isoleucine |
| | valine |
| Aromatic | phenylalanine |
| | tryptophan |
| | tyrosine |
| Small | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the endoglucanase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e mannanase activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO95/17413, or WO 95/22625.

Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 226 to 490 of SEQ ID NO: 2 and retain the endoglucanase activity of the wild-type protein.

The endoglucanase enzyme of the invention may, in addition to the enzyme core comprising the catalytically domain, also comprise a cellulose binding domain (CBD), the cellulose binding domain and enzyme core (the catalytically active domain) of the enzyme being operably linked. The cellulose binding domain (CBD) may exist as an integral part the encoded enzyme, or a CBD from another origin may be introduced into the endoglucanase thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I–X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the endoglucanase and growing the host cell to express the fused gene. Enzyme hybrids may be described by the following formula:

CBD-MR-X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to to about 100 amino acids, more preferably of from 2 to 40 amino acids; and X is an N-terminal or C-terminal region of a polypeptide encoded by the first or second DNA sequence of the invention.

In a preferred embodiment, the isolated polynucleotide molecule of the invention further comprises a partial DNA sequence encoding a cellulose binding domain (CBD). An example of such a partial DNA sequence is the sequence corresponding to the nucleotides in positions 60–435 of SEQ ID NO:1 or the CBD encoding part of the DNA sequence cloned into the plasmid pSJ1678 present in *Escherichia coli*, DSM 11476. The isolated polynucleotide molecule of the invention may comprise a further partial nucleotide sequence encoding a linking region, the linking region operably linking the cellulose binding domain (CBD) and the catalytically active domain (CAD) of the enzyme encoded by the nucleotide sequence comprised by the isolated polynucleotide molecule. Preferably, the linking region consists of from about 2 amino acid residues to about 120 amino acid residues, especially 10–80 amino acid residues.

The polynucleotide molecules of the invention including the partial DNA sequences described above can be cloned from the strain *Escherichia coli* DSM 11476 using standard methods e.g. as described by Sambrook et al., (1989), Molecular Cloning: A Laboratory Manual. Cold Spring Harbor Lab.; Cold Spring Harbor, N.Y.

The polynucleotide molecules of the invention and partial DNA sequences thereof can also be cloned by any general method involving cloning, in suitable vectors, a DNA library from any organism, preferably a prokaryot, more preferably from a bacterium, more preferably from a gram positive bacterium, especially from a strain belonging to the class Actinomycetes, more especially from the family Pseudonocardiaceae, for example from the genus Saccharothrix, especially from *Saccharothrix australiensis*, expected to produce the endo-β-1,4-glucanase of interest, transforming suitable host cells with said vectors, culturing the host cells under suitable conditions to express any enzyme of interest encoded by a clone in the DNA library, screening for positive clones by determining any cellulolytic activity of the enzyme produced by such clones, and isolating the enzyme encoding DNA from such clones.

Alternatively, the DNA encoding a cellulase of the invention may, in accordance with well-known procedures, conveniently be cloned from a suitable source, such as any of the below mentioned organisms, by use of synthetic oligonucleotide probes prepared on the basis of the DNA sequence obtainable from the plasmid present in *Escherichia coli* DSM 11476.

How to use a sequence of the invention to get other related sequences: The disclosed sequence information herein relating to a polynucleotide sequence encoding an endo-beta-1,4-glucanase of the invention can be used as a tool to identify other homologous mannanases. For instance, polymerase chain reaction (PCR) can be used to amplify sequences encoding other homologous mannanases from a variety of microbial sources, in particular of different Saccharothrix species.

Immunological cross-reactivity

Polyclonal antibodies, especially monospecific polyclonal antibodies, to be used in determining immunological cross-reactivity may be prepared by use of a purified cellulolytic enzyme. More specifically, antiserum against the endoglucanase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation (($NH_4$)$_2SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Microbial Sources

For the purpose of the present invention the term "obtained from" or "obtainable from" as used herein in connection with a specific source, means that the enzyme is produced or can be produced by the specific source, or by a cell in which a gene from the source have been inserted.

It is at present contemplated that the cellulase of the invention may be obtained from a gram positive bacterium belonging to the family Pseudonocardiaceae, in particular a strain of the genus Saccharothrix, in particular a strain of *Saccharothrix australiensis.*

In a preferred embodiment, the cellulase of the invention is obtained from the strain *Saccharothrix australiensis,* IFO 14444. It is at present contemplated that a DNA sequence encoding an enzyme homologous to the enzyme of the invention may be obtained from other strains belonging to the genus Saccharothrix.

An isolate of a strain of *Saccharothrix australiensis* from which an endo-β-1,4-glucanase of the invention can be derived is publicly available from Institute for Fermentation (IFO), 17-85 Juso-honmachi 2-chome, Yodogawa-ku, Osaka 532, Japan, under the deposition number IFO 14444.

Further, the plasmid pSJ1678 comprising the DNA sequence encoding the endoglucanase of the invention has been transformed into a strain of the *Escherichia coli* and deposited under the deposition number DSM 11476.

Recombinant expression vectors

A recombinant vector comprising a DNA construct encoding the enzyme of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gen, or the *Bacillus pumilus* xylosidase gene, or the phage Lambda PR or PL promoters or the *E. coli* lac, trD or tac promoters.

The DNA sequence encoding the enzyme of the invention may be also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host cells

The cloned DNA molecule introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the cloned DNA molelcule or the recombinant vector of the invention is introduced may be any cell which is capable of producing the desired enzyme and includes bacteria, yeast, fungi and higher eukaryotic cells.

Examples of bacterial host cells which on cultivation are capable of producing the enzyme of the invention may be a gram-positive bacteria such as a strain of Bacillus, in particular *Bacillus alkalophilus, Bacillus amyloliquefaciens, Bacillus brevis, Bacillus lautus, Bacillus lentus, Bacillus licheniformis, Bacillus circulans, Bacillus coagulans, Bacillus megatherium, Bacillus stearothermophilus, Bacillus subtilis* and *Bacillus thuringiensis,* a strain of Lactobacillus, a strain of Streptococcus, a strain of Streptomyces, in particular *Streptomyces lividans* and *Streptomyces murinus,* or the host cell may be a gram-negative bacteria such as a strain of *Escherichia coli.*

The transformation of the bacteria may be effected by protoplast transformation, electroporation, conjugation, or by using competent cells in a manner known per se (cf. e.g. Sambrook et al., supra).

When expressing the enzyme in a bacteria such as *Escherichia coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in a gram-positive bacteria such as a strain of Bacillus or a strain of Streptomyces, the enzyme may be retained in the cytoplasm, or may be directed to the extracellular medium by a bacterial secretion sequence.

Examples of a fungal host cell which on cultivation are capable of producing the enzyme of the invention is e.g. a strain of Aspergillus or Fusarium, in particular *Aspergillus awamori, Aspergillus nidulans, Aspergillus niger, Aspergillus oryzae,* and *Fusarium oxysporum,* and a strain of Trichoderma, preferably *Trichoderma harzianum, Trichoderma reesei* and *Trichoderma viride.*

Fungal cells may be transformed by a process involving protoplast formation and transformation of the protoplasts followed by regeneration of the cell wall in a manner known per se. The use of a strain of Aspergillus as a host cell is described in EP 238 023 (Novo Nordisk A/S), the contents of which are hereby incorporated by reference.

Examples of a host cell of yeast origin which on cultivation are capable of producing the enzyme of the invention is e.g. a strain of Hansenula sp., a strain of Kluyveromyces sp., in particular *Kluyveromyces lactis* and *Kluyveromyces marcianus,* a strain of Pichia sp., a strain of Saccharomyces, in particular *Saccharomyces carlsbergensis, Saccharomyces cerevisae, Saccharomyces kluyveri* and *Saccharomyces uvarum, a strain of Schizosaccharomyces sp., in particular Schizosaccharomyces pombe,* and a strain of Yarrowia sp., in particular *Yarrowia lipolytica.*

Examples of a host cell of plant origin which on cultivation are capable of producing the enzyme of the invention is e.g. a plant cell of *Solanum tuberosum* or *Nicotiana tabacum.*

Method of producing a cellulolytic enzyme

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

As defined herein, an isolated polypeptide (e.g. an enzyme) is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The term "isolated polypeptide" may alternatively be termed "purified polypeptide".

When an expression vector comprising a DNA sequence encoding the enzyme is transformed into a heterologous host cell it is possible to enable heterologous recombinant production of the enzyme of the invention.

Thereby it is possible to make a highly purified or monocomponent cellulolytic composition, characterized in being free from homologous impurities.

In this context homologous impurities means any impurities (e.g. other polypeptides than the enzyme of the invention) which originate from the homologous cell where the enzyme of the invention is originally obtained from.

In the present invention the homologous host cell may be a strain of *Saccharothrix australiensis.*

The medium used to culture the transformed host cells may be any conventional medium suitable for growing the host cells in question. The expressed cellulolytic enzyme may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Enzyme compositions

In a still further aspect, the present invention relates to an enzyme composition comprising an enzyme exhibiting cellulolytic activity as described above.

The enzyme composition of the invention may, in addition to the cellulase of the invention, comprise one or more other enzyme types, for instance hemicellulase such as xylanase and mannanase, other cellulase or endo-$\beta$-1,4-glucanase components, chitinase, lipase, esterase, pectinase, cutinase, phytase, oxi-doreductase (peroxidase, haloperoxidase, oxidase, laccase), protease, amylase, reductase, phenoloxidase, ligninase, pullulanase, pectate lyase, xyloglucanase, pectin acetyl esterase, polygalacturonase, rhamnogalacturonase, pectin lyase, pectin methylesterase, cellobiohydrolase, transglutaminase; or mixtures thereof.

The enzyme composition may be prepared in accordance with methods known in the art and may be in the form of a liquid or a dry composition. For instance, the enzyme composition may be in the form of a granulate or a microgranulate. The enzyme to be included in the composition may be stabilized in accordance with methods known in the art.

Endoglucanases have potential uses in a lot of different industries and applications. Examples are given below of preferred uses of the enzyme composition of the invention. The dosage of the enzyme composition of the invention and other conditions under which the composition is used may be determined on the basis of methods known in the art.

The enzyme composition according to the invention may be useful for at least one of the following purposes.

Uses

During washing and wearing, dyestuff from dyed fabrics or garment will conventionally bleed from the fabric which then looks faded and worn. Removal of surface fibers from the fabric will partly restore the original colours and looks of the fabric. By the term "colour clarification", as used herein, is meant the partly restoration of the initial colours of fabric or garment throughout multiple washing cycles.

The term "de-pilling" denotes removing of pills from the fabric surface.

The term "soaking liquor" denotes an aqueous liquor in which laundry may be immersed prior to being subjected to a conventional washing process. The soaking liquor may contain one or more ingredients conventionally used in a washing or laundering process.

The term "washing liquor" denotes an aqueous liquor in which laundry is subjected to a washing process, i.e. usually a combined chemical and mechanical action either manually or in a washing machine. Conventionally, the washing liquor is an aqueous solution of a powder or liquid detergent composition.

The term "rinsing liquor" denotes an aqueous liquor in which laundry is immersed and treated, conventionally immediately after being subjected to a washing process, in order to rinse the laundry, i.e. essentially remove the detergent solution from the laundry. The rinsing liquor may contain a fabric conditioning or softening composition.

The laundry subjected to the method of the present invention may be conventional washable laundry. Preferably, the major part of the laundry is sewn or unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, flax/linen, jute, cellulose acetate fibers, lyocell).

DETERGENT DISCLOSURE AND EXAMPLES
Surfactant system

The detergent compositions according to the present invention comprise a surfactant system, wherein the surfactant can be selected from nonionic and/or anionic and/or cationic and/or ampholytic and/or zwitterionic and/or semipolar surfactants.

The surfactant is typically present at a level from 0.1% to 60% by weight.

The surfactant is preferably formulated to be compatible with enzyme components present in the composition. In liquid or is gel compositions the surfactant is most preferably formulated in such a way that it promotes, or at least does not degrade, the stability of any enzyme in these compositions.

Preferred systems to be used according to the present inven-tion comprise as a surfactant one or more of the nonionic and/or anionic surfactants described herein.

Polyethylene, polypropylene, and polybutylene oxide conden-sates of alkyl phenols are suitable for use as the nonionic surfactant of the surfactant systems of the present inven-tion, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050, (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of the surfactant systems of the present invention are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula

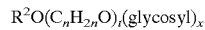

$R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, pre-ferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula RO(A)$_m$SO3M wherein R is an unsubstituted $C_{10}$-$C_{-24}$ alkyl or hydroxyalkyl group having a $C_{10}$–$C_{24}$ alkyl component, preferably a $C_{12}$–$C_{20}$ alkyl or hydro-xyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethylammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}$E(1.0)M), $C_{12}$–$C_{18}$ alkyl polyethoxylate (2.25) sulfate ($C_{12}$–$C_{18}$(2.25)M, and $C_{12}$–$C_{18}$ alkyl polyethoxylate (3.0) sulfate ($C_{12}$–$C_{18}$E(3.0)M), and $C_{12}$–$C_{18}$ alkyl polyethoxylate (4.0) sulfate ($C_{12}$–$C_{18}$E(4.0) M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

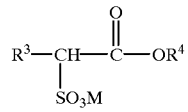

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula ROSO3M wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16}$–$C_{18}$ alkyl chains are preferred for higher wash temperatures (e.g. above about 50° C.).

Other anionic surfactants useful for detersive purposes can also be included in the laundry detergent compositions of the present invention. Theses can include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$— M+ wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

$$[R^2(OR^3)_y][R^4(OR^3)_y]_2R^5N+X-$$

wherein $R^2$ is an alkyl or alkyl benzyl group having from about 8 to about 18 carbon atoms in the alkyl chain, each $R^3$ is selected form the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula:

$$R_1R_2R_3R_4N^+X^- \qquad (i)$$

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{40})_xH$ where x has a value from 2 to 5, and X is an anion. Not more than one of $R_2$, $R_3$ or $R_4$ should be benzyl.

The preferred alkyl chain length for $R_1$ is $C_{12}$–$C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:

coconut trimethyl ammonium chloride or bromide;

coconut methyl dihydroxyethyl ammonium chloride or bromide;

decyl triethyl ammonium chloride;

decyl dimethyl hydroxyethyl ammonium chloride or bromide;

$C_{12-15}$ dimethyl hydroxyethyl ammonium chloride or bromide;

coconut dimethyl hydroxyethyl ammonium chloride or bromide;

myristyl trimethyl ammonium methyl sulphate;

lauryl dimethyl benzyl ammonium chloride or bromide;

lauryl dimethyl (ethenoxy)$_4$ ammonium chloride or bromide;

choline esters (compounds of formula (i) wherein $R_1$ is

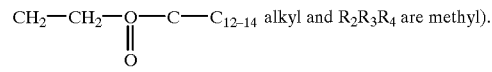

di-alkyl imidazolines [compounds of formula (i)].

Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

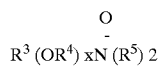

$$R^3(OR^4)xN(R^5)_2$$

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder system

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686, and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2,-ethane tetracarboxylates, 1,1,3,3-propane tetrac7arboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadien-ide pentacarboxylates, 2,3,4,5-tetrahydro-furan-cis, cis, cis-tetracarboxylates, 2,5-tetrahydro-furan-cis, discarboxylates, 2,2,5,5,-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxy-carboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the enzyme preparation of the invention, comprise other enzyme (s) which provides cleaning performance and/or fabric care benefits.

Such enzymes include proteases, lipases, cutinases, amylases, cellulases, peroxidases, oxidases (e.g. laccases).

Proteases

Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Preferred commercially available protease enzymes include those sold under the trade names Alcalase, Savinase, Primase, Durazym, and Esperase by Novo Nordisk A/S (Denmark), those sold under the tradename Maxatase, Maxacal, Maxapem, Properase, Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases

Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a Pseudomonas lipase such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, a *P. fluorescens* lipase, a Bacillus lipase, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446).

Especially suitable lipases are lipases such as M1 Lipase™, Luma fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases

Any amylase (a and/or b) suitable for use in alkaline solutions can be used. Suitable amylases include those of bacterial or fungal origin. Chemically or genetically modified mutants are included. Amylases include, for example, a-amylases obtained from a special strain of *B. licheniformis*, described in more detail in GB 1,296,839. Commercially available amylases are Duramyl™, Termamyl™, Fungamyl™ and BAN™ (available from Novo Nordisk A/S) and Rapidase™ and Maxamyl P™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases

Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307 which discloses fungal cellulases produced from *Humicola insolens*, in WO 96/34108 and WO 96/34092 which disclose bacterial alkalophilic cellulases (BCE 103) from Bacillus, and in WO 94/21801, U.S. Pat. No. 5,475,101 and U.S. Pat. No. 5,419,778 which disclose EG III cellulases from Trichoderma. Especially suitable cellulases are the cellulases having colour care benefits. Examples of such cellulases are cellulases described in European patent application No. 0 495 257 and the endoglucanase of the present invention. Commercially available cellulases include Celluzyme™ and Carezyme™ produced by a strain of *Humicola insolens* (Novo Nordisk A/S), KAC-500(B)™ (Kao Corporation), and Puradax™ (Genencor International).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases

Peroxidase enzymes are used in combination with hydrogen peroxide or a source thereof (e.g. a percarbonate, perborate or persulfate). Oxidase enzymes are used in combination with oxygen. Both types of enzymes are used for "solution bleaching", i.e. to prevent transfer of a textile dye from a dyed fabric to another fabric when said fabrics are washed together in a wash liquor, preferably together with an enhancing agent as described in e.g. WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching agents

Additional optional detergent ingredients that can be included in the detergent compositions of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, U.S. Pat. No. 740,446, EP 0 133 354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetra-acetylethylenediamine (TAED), nonanoyloxybenzene-sulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Ser. No. 08/136,626.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and-/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", Nature 369, 1994, pp. 637–639.

Suds suppressors

Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or waterdispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/silica mixture in combination with fumed nonporous silica such as Aerosil®.

The suds suppressors described above are normally employed at levels of from 0.001% to 2% by weight of the composition, preferably from 0.01% to 1% by weight.

Other components

Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2' disulphonate, disodium 4, -4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4',4"-bis-(2,4-dianilino-s-tri-azin-6 ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2, 1,3-triazol-2-yl)-stilbene-2,2' disulphonate, di-so-dium 4,4'bis(2-anilino-4-(1-methyl-2-hydroxyethylamino)-s-triazin-6-ylami-no)stilbene-2,2'disulphonate, sodium 2(stilbyl-4"-(naphtho-1',2':4,5)-1,2,3,-triazole-2"-sulphonate and 4,4'-bis(2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

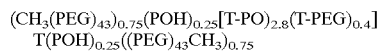

$(CH_3(PEG)_{43})_{0.75}(POH)_{0.25}[T-PO]_{2.8}(T-PEG)_{0.4}]$
$T(POH)_{0.25}((PEG)_{43}CH_3)_{0.75}$ where PEG is —$(OC_2H_4)O$-, PO is $(OC_3H_6O)$ and T is $(pOOC_6H_4CO)$.

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secon-darily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening agents

Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono $C_{12}$-$C_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric dye-transfer inhibiting agents

The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinyl-pyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to is 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention. In the detergent compositions, the abbreviated component identifications have the following meanings:

| | |
|---|---|
| LAS: | Sodium linear $C_{12}$ alkyl benzene sulphonate |
| TAS: | Sodium tallow alkyl sulphate |
| XYAS: | Sodium $C_{1X}$–$C_{1Y}$ alkyl sulfate |
| SS: | Secondary soap surfactant of formula 2-butyl octanoic acid |
| 25EY: | A $C_{12}$–$C_{15}$ predominantly linear primary alcohol condensed with an average of Y moles of ethylene oxide |
| 45EY: | A $C_{14}$–$C_{15}$ predominantly linear primary alcohol condensed with an average of Y moles of ethylene oxide |
| XYEZS: | $C_{1X}$–$C_{1Y}$ sodium alkyl sulfate condensed with an average of Z moles of ethylene oxide per mole |
| Nonionic: | $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh |
| CFAA: | $C_{12}$–$C_{14}$ alkyl N-methyl glucamide |
| TFAA: | $C_{16}$–$C_{18}$ alkyl N-methyl glucamide |
| Silicate: | Amorphous Sodium Silicate ($SiO_2$:$Na_2O$ ratio = 2.0) |
| NaSKS-6: | Crystalline layered silicate of formula d-$Na_2Si_2O_5$ |
| Carbonate: | Anhydrous sodium carbonate |
| Phosphate: | Sodium tripolyphosphate |
| MA/AA: | Copolymer of 1:4 maleic/acrylic acid, average molecular weight about 80,000 |
| Polyacrylate: | Polyacrylate homopolymer with an average molecular weight of 8,000 sold under the tradename PA30 by BASF GmbH |
| Zeolite A: | Hydrated Sodium Aluminosilicate of formula $Na_{12}(AlO_2SiO_2)_{12}.27H_2O$ having a primary particle size in the range from 1 to 10 micrometers |
| Citrate: | Tri-sodium citrate dihydrate |
| Citric: | Citric Acid |
| Perborate: | Anhydrous sodium perborate monohydrate bleach, empirical formula $NaBO_2.H_2O_2$ |
| PB4: | Anhydrous sodium perborate tetrahydrate |
| Percarbonate: | Anhydrous sodium percarbonate bleach of empirical formula $2Na_2CO_3.3H_2O_2$ |
| TAED: | Tetraacetyl ethylene diamine |
| CMC: | Sodium carboxymethyl cellulose |
| DETPMP: | Diethylene triamine penta (methylene phosphonic acid), marketed by Monsanto under the Tradename Dequest 2060 |
| PVP: | Polyvinylpyrrolidone polymer |
| EDDS: | Ethylenediamine-N,N'-disuccinic acid, [S,S] isomer in the form of the sodium salt |

| Suds Suppressor: | 25% paraffin wax Mpt 50° C., 17% hydrophobic silica, 58% paraffin oil |
|---|---|
| Granular Suds suppressor: | 12% Silicone/silica, 18% stearyl alcohol 70% starch in granular form |
| Sulphate: | Anhydrous sodium sulphate |
| HMWPEO: | High molecular weight polyethylene oxide |
| TAE 25: | Tallow alcohol ethoxylate (25) |

Detergent Example I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

|  | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

Textile applications

In another embodiment, the present invention relates to use of the endoglucanase of the invention in the bio-polishing process. Bio-Polishing is a specific treatment of the yarn surface which improves fabric quality with respect to handle and appearance without loss of fabric wettability. The most important effects of Bio-Polishing can be characterized by less fuzz and pilling, increased gloss/luster, improved fabric handle, increased durable softness and altered water absorbency. Bio-Polishing usually takes place in the wet processing of the manufacture of knitted and woven fabrics. Wet processing comprises such steps as e.g. desizing, scouring, bleaching, washing, dying/printing and finishing. During each of these steps, the fabric is more or less subjected to mechanical action. In general, after the textiles have been knitted or woven, the fabric proceeds to a desizing stage, followed by a scouring stage, etc. Desizing is the act of removing size from textiles. Prior to weaving on mechanical looms, warp yarns are often coated with size starch or starch derivatives in order to increase their tensile strength. After weaving, the size coating must be removed before further processing the fabric in order to ensure a homogeneous and wash-proof result. It is known that in order to achieve the effects of Bio-Polishing, a combination of cellulytic and mechanical action is required. It is also known that "super-softness" is achievable when the treatment with a cellulase is combined with a conventional treatment with softening agents. It is contemplated that use of the endoglucanase of the invention for bio-polishing of cellulosic fabrics is advantageous, e.g. a more thorough polishing can be achieved. Bio-polishing may be obtained by applying the method described e.g. in WO 93/20278.

Stone-washing

It is known to provide a "stone-washed" look (localized abrasion of the colour) in dyed fabric, especially in denim fabric or jeans, either by washing the denim or jeans made from such fabric in the presence of pumice stones to provide the desired localized lightening of the colour of the fabric or by treating the fabric enzymatically, in particular with cellulytic enzymes. The treatment with an endoglucanase of the present invention may be carried out either alone such as disclosed in U.S. Pat. No. 4,832,864, together with a smaller amount of pumice than required in the traditional process, or together with perlite such as disclosed in WO 95/09225.

Materials and Methods

Organisms:

Saccharothrix australiensis, IFO 14444, comprises the cellulase encoding DNA sequence of the invention.

Escherichia coli, DSM 11476, containing the plasmid comprising the DNA sequence encoding the cellulolytic enzyme of the invention, in the cloning vector pSJ1678.

Other strains:

E. coli strain: Cells of E. coli SJ2 (Diderichsen, B. et al. (1990)), were prepared for and transformed by electroporation using a Gene Pulser™ electroporator from BIO-RAD as described by the supplier.

Plasmids:

pSJ1678 (see WO 94/19454 which is hereby incorporated by reference).

General molecular biology methods:

DNA manipulations and transformations were performed using standard methods of molecular biology (Sambrook et al, (1989); Ausubel et al., (1995); Harwood et al., (1990)).

Enzymes for DNA manipulations were used according to the specifications of the suppliers.

Isolation of the DNA sequence encoding the cellulolytic enzyme of the invention:

The DNA sequence, comprising the DNA sequence shown in SEQ ID No. 1, encoding the endoglucanase of the invention, can be obtained from the deposited organism E. coli, DSM 11476, by extraction of plasmid DNA by methods known in the art (Sambrook et al. (1989)).

Cloning of the Saccharothrix australiensis endo-β-1,4-glucanase gene

Genomic DNA preparation:

Strain Saccharothrix australiensis, IFO 14444, was propagated on TY-agar medium at 30° C. for 2–3 days. Cells were harvested by scraping them of the plates, and genomic DNA isolated by the method described by Pitcher et al. (1989). The only modification to the published method is the adding of Mutanolysin (Cataloge no. M-9901, SIGMA, USA) of 30 ug/ml to the lysis buffer originally only containing lysozyme.

Genomic library construction:

Genomic DNA was partially digested with restriction enzyme Sau3A, and size-fractionated by electrophoresis on a 0.7% agarose gel. Fragments between 2 and 7 kb in size were isolated by electrophoresis onto DEAE-cellulose paper (Dretzen et al., (1981)).

Isolated DNA fragments were ligated to BamHI digested pSJ1678 plasmid DNA, and the ligation mixture was used to transform E. coli SJ2.

Cells were plated on LB agar plates containing 0.1% CMC (Sodium-Carboxy-Methyl-Cellulose, Aqualon, France) and 9 µg/ml Chloramphenicol and incubated overnight at 37° C.

Identification of positive clones by colony hybridization

A DNA library in E. coli, constructed as described above, was screened on LB agar plates containing 0.1% CMC (Sodium-Carboxy-Methyl-Cellulose, Aqualon, France) and 9 µg/ml Chloramphenicol and incubated overnight at 37° C. The transformants were subsequently replica plated onto the same type of plates, and these new plates were incubated 8 hours or overnight at 37° C.

The original plates were coloured using 1 mg/ml of Congo Red (SIGMA, USA). The coloring was continued for half an hour with moderate orbital shaking, after which the plates were washed two times 15 minutes using 1 M NaCl.

Yellowish halos appeared at positions where cellulase positive clones were present, from the replica plates these cellulase positive clones were rescued and restreaked onto LB agar plates containing 0.1% CMC and 9 µg/ml Chloramphenicol and incubated overnight at 37° C.

Characterization of positive clones:

From the restreaking plates the endoglucanase positive clones were obtained as single colonies, and plasmids were extracted. Phenotypes were confirmed by retransformation of E.coli SJ2, and plasmids characterized by restriction digests.

The endoglucanase gene was characterized by DNA sequencing using the Taq deoxy-terminal cycle sequencing kit (Perkin-Elmer, USA), fluorescent labeled terminators and 5 pmol of the primer #3507:

5'-GGC TTT TAA GCC GTC TGT ACG-3' (SEQ ID NO:3).

In another reaction the nucleotide sequence was determined using the primer #8392:

5'-CTC ACG TTA AGG GAT TTT GGT CTG G-3' (SEQ ID NO:4)

Analysis of the sequence data was performed according to Devereux et al., (1984). The sequence corresponds to the DNA sequence shown in SEQ ID No 1. This first DNA sequences derived in this way was used to design new primers for further sequencing of the endoglucanase gene, and again new primers were designed, used for sequencing and so forth.

Media

TY and LB agar (as described in Ausubel et al.,(1995)).

Determination of cellulolytic activity

The cellulolytic activity of endoglucanase is determined relative to an analytical standard and may be expressed in the unit ECU.

Cellulolytic enzymes hydrolyse CMC, thereby decreasing the viscosity of the incubation mixture. The resulting reduction in viscosity may be determined by a vibration viscosimeter (e.g. MIVI 3000 from Sofraser, France).

Determination of the cellulolytic activity, measured in terms of ECU, may be determined according to the analysis method AF 301.1 which is available from the Applicant upon request.

The ECU assay quantifies the amount of catalytic activity present in the sample by measuring the ability of the sample to reduce the viscosity of a solution of carboxymethylcellulose (CMC). The assay is carried out at 40° C., pH 7.5 using a relative enzyme standard for reducing the viscosity of the CMC substrate.

The following non-limiting examples illustrate the invention.

Example 1

Cloning and expression of an endo-β-1,4-glucanase from Saccharothrix australiensis, IFO 14444

Preparation of genomic DNA from Saccharothrix australiensis, IFO 14444, cloning of the endoglucanase gene and DNA sequencing was performed as described in Materials and Methods. One positive transformant isolated was DSM 11476, containing the plasmid pSJ1678 containing an insert of approximately 2.300 base-pairs. This insert was partially DNA sequenced, and revealed the presence of the sequence of an endoglucanase-encoding gene. According to the classification of glycosyl hydrolases (Henrissat et al., (1993)) the endoglucanase belongs to the family 6 of glycosyl hydrolases.

The nucleotide sequence is designated SEQ ID NO 1.

The DNA corresponding to the endo-β-1,4-glucanase gene is obtainable from the plasmid obtainable from the strain deposited as DSM 11476.

Example 2

Endo-β-1,4-glucanase from various Saccharothrix strains

The following strains were tested:

Saccharothrix texasensis, NRRL B-16134,

Saccharothrix waywayandensis, NRRL B-16159,

Saccharothrix cryophilis, NRRL B-16238,

Saccharothrix sp., IFO 13785,

Saccharothrix flava, ATCC 29533,

Saccharothrix coeruleofusca, ATCC 35108,

Saccharothrix longispora, ATCC 31109,

Saccharothrix mutabilis ssp. mutabilis, ATCC 31520,

Saccharothrix aerocolonigenes, ATCC 23870,

Saccharothrix mutabilis ssp. capreolus, ATCC 23892,

Saccharothrix syringae, DSM 43886.

A. Southern hybridization test of Saccharothrix strains

Genomic DNA preparation

Each Saccharothrix strain (see above) was propagated on TY-agar medium supplemented with 2% soluble starch at 25° C. for 3–4 days. Cells were harvested, and genomic DNA isolated by the method described by Pitcher et al. (Pitcher, D. G., Saunders, N. A., Owen, R. J. (1989). Rapid extraction of bacterial genomic DNA with guanidium thiocyanate. Lett. Appl. Microbiol., 8, 151–156).

Hybridization conditions

Suitable conditions for determining hybridization between a nucleotide probe and a homologous DNA or RNA sequence involves presoaking of the filter containing the DNA fragments or RNA to hybridize in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 μg/ml of denatured sonicated salmon sperm DNA (Sambrook et al. 1989), followed by hybridization in the same solution containing a random-primed (Feinberg, A. P. and Vogelstein, B. (1983) Anal. Biochem. 132:6–13), $^{32}$P-dCTP-labeled (specific activity>1×10$^9$ cpm/μg) probe for 12 hours at ca. 45° C. The filter is then washed two times for 30 minutes in 2×SSC, 0.5% SDS at preferably at least 55° C., more preferably at least 60° C., more preferably at least 65° C., even more preferably at least 70° C., especially at least 75° C.

Experimental

Probe:

2.5 kb fragment from pMB145 (Saccharothrix australiensis, IFO 14444).

Result: All strains hybridized to BamHI.

Accordingly, all strains produce endo-β-1,4-glucanase belonging to family 6.

B. CMC-Congo Red Assay of Saccharothrix strains (identification of positive clones by colony hybridization)

Method:

Strains were grown on wheat bran medium (w. bran 4%, y. ext. 0.1% and agar 1.5%) at 30° C. for 4 days. Agar plugs were placed on CMC assay plates (basal: CMC 0.1%, agar 1.5%) at various pHs (pH 5, 7, 9, 10). LAS (linear alkyl sulfate) was added to the final conc. of 0.1%. AZCL-HE was used at pH 7. Incubation was carried out at 40° C., overnight. Then the plate was stained with Congo Red and the diameter of clearing zones (mm) were measured.

Results (diameter in mm):

| Source | AZCl-HE | pH 7 | pH 9 |
|---|---|---|---|
| IFO 14444 | 12 | 17 | 13 |
| NRRL B-16134 | 10 | 17 | 15 |
| NRRL B-16159 | 9 | 13 | 12 |
| NRRL B-16238 | — | 9 | — |
| IFO 13785 | 22 | 23 | 16 |
| ATCC 29533 | 8 | 9 | — |
| ATCC 35108 | 13 | 16 | 15 |

-continued

| Source | AZCl-HE | pH 7 | pH 9 |
|---|---|---|---|
| ATCC 31109 | 13 | 18 | 10 |
| ATCC 31520 | 18 | 21 | 16 |
| ATCC 23870 | 13 | 16 | 10 |
| ATCC 23892 | 13 | 16 | 13 |
| DSM 43886 | 12 | 16 | 13 |

Example 3
Purification and characterization of an endo-β-1,4-glucanase from *Saccharothrix australiensis*, IFO 14444

The plasmid of example 1 was inserted into *E. coli* JM 109. The *E. coli* strain was grown in super broth (pancreatic digest of casein 32 g/l, yeast extract 20 g/l and NaCl 5 gram/l adjusted to pH 7.0) at 37° C. for one day. Cells were collected and lysed by sonication. The supernatant was freeze dried. 24 gram was obtained from 13 l of fermentation with a total activity of 4600 ECU.

Purification:

The powder was diluted in ion exchanged water total of 175 ml. Using 50 gram of Avicel at 4° C., on a column 50 mM phosphate buffer pH 7.5 and washed using high salt (0.5 M NaCl in the same buffer). The enzyme eluted using ion exchanged pure water. Total 2550 ECU was obtained. The sample still contained some color and was further purified using ion exchange chromatography. A HPQ column equilibrated with 50 mM Tris pH 7.5 was used for binding of the enzyme and the color eluted the pure enzyme was eluted using a NaCl gradient.

Characterization:

The purified protein gave a single band in SDS-PAGE of 50 kDa with a pI of around 3.7.

The specific activity on ECU was 50 ECU per mg of protein. A molar extinction value of 113380 was based on the amino acid composition and was used for determination of the protein concentration after a ratio of 1.8 (E280/E260) was obtained and using the MW of 50 kDa.

Catalytic activity on phosphoric acid swollen cellulose at pH 8.5 was apparent kcat of 22 per sec and apparent KM of 0.6 g/l. The cellulase has no activity on PNP-beta cellobioside.

Buffers

All enzyme experiments were performed in one of the following buffers:

| pH 3.0 to 3.5 | 0.1 M sodium citrate |
| pH 4.0 to 5.5 | 0.1 M sodium acetate |
| pH 6.0 | 0.1 M sodium MES buffer |
| pH 6.5 to 7.5 | 0.1 M sodium MOPS buffer |
| pH 8.0 to 8.5 | 0.1 M Barbital buffer |
| pH 9.0 to 10.0 | 0.1 M Glycine buffer | pH activity profiles

The pH activity profiles were obtained using CMC. The final CMC concentration was 7.5 gram per liter, incubation was for 20 min at 40° C. and the formation of reducing sugars determined by using p-hydroxy-benzoic-acid-hydrazide (PHBAH) modified from Lever (1972) using 5 g of potassium sodium tartrate in addition to 1.5 g of PHBAH. The pH optimum was 8.0, and more than 50% relative activity was obtained between pH 6.5 and 9.0.

Apparent kinetic constant determination using phosphoric-acid swollen cellulose (PASC)

PASC stock solution was prepared as follows: 5 g of cellulose (Avicel) was moistened with water, and 150 ml ice cold 85% ortho-phosphoric-acid was added. The suspension was slowly stirred in an ice-bath for 1 h. Then 100 ml ice cold acetone was added while stirring. The slurry was transfered to a Buchner filter with Pyrex sintered disc number 3 and then washed three times with 100 ml ice cold acetone, sucked as dry as possible after each wash. Finally it was washed twice with 500 ml water, and again sucked as dry as possible after each wash. The PASC was mixed with deionized water to a total volume of 300 ml. It was blended to homogeneity (using an Ultra Turrax Homogenizer) and stored in a refrigerator for up to one month.

Substrate was equilibrated with buffer using the following procedure: 20 g phosphoric-acid swollen cellulose PASC stock solution was centrifuged for 20 min at 5000 rpm, the supernatant was poured off, and the sediment was resuspended in 30 ml of buffer. After 20 min centrifugation at 5000 rpm, the supernatant was decanted, and the sediment was resuspended in buffer to a total of 30 g. This corresponds to a substrate concentration of 10 mg $l^{-1}$.

To measure kinetic parameters, substrate concentrations from 0.2 mg $ml^{-1}$ to 8 mg $ml^{-1}$ were used. Rates were measured at 8 different substrate concentrations in duplicate. The amount of reducing sugars was determined using the PHBAH method modified from Lever (1972).

The enzyme concentration was calculated using the molar absorbancy. The apparent kinetic constants $K_{M(app.)}$, $V_{max\,(app.)}$ and $k_{cat(app.)}$ were calculated using the equation for enzyme kinetics in the computer program GraFit (Leatherbarrow, 1992).

Example 4
Tensile strength loss induced by treating fabric with endo-β-1,4-glucanase from *Saccharothrix australiensis*, IFO 14444

Tensile strength loss induced by treating textile with the purified endoglucanase from example 3 was measured and compared with a fungal family 6 endoglucanase.

Experimental protocol:

| Buffer | 0.05 M phosphate buffer pH 7.0 |
| Volume | 100 ml |
| Temperature | room temperature |
| Textile | Tea towels pre-aged ED 9613829 5 pieces a 5 × 25 cm |
| Dosage | 2x0, 1000, 10.000, 100.000 ECU/1 Carezyme 1900, 19.000, 190.000 ECU/1 of family 6 cellulases |
| Time | 7 days dark storage |
| Rinse time | 10 min. in running tap water |
| Evaluation | Tensile strength loss measured on an Instron instrument 5564. Breakage within 20+/−3 sec. |

Pre-aged fabric was incubated for a week with different dosages of enzyme in phosphate buffer pH 7.0. Afterwards the fabric was rinsed in water, acclimatised in climate room for 24 hours (60% RH, 20° C.). Tensile strength was measured on an Instron instrument. The tensile strength loss is calculated relative to pre-aged textile which has not been incubated (reference). Blank (no enzyme) and the EG VI from the fungus Humicola insolens (family 6 endoglucanase) were included in the experiment for comparison.

| | ECU/1 | % TSL |
|---|---|---|
| Reference | | 0 |
| Blank | 0 | −3.6 |
| Fungal EG VI | 19,000 | 1.2 |
| | 190,000 | 12.5 |

-continued

| Enzyme | ECU/1 | % TSL |
|---|---|---|
| Enzyme of the invention | 59,100 | −6.7 |

The enzyme of the invention gave not rise to any tensile strength loss.

Example 5

Colour Clarification in Terg-O-Meter

In this example the capability of the endoglucanase of the invention to rejuvenate the colour of cotton textile is demonstrated using an assay for determining colour care benefits, i.e. "Color Clarification", of cotton cloth in a miniaturised washing machine, the 100 ml Terg-O-Meter.

250 ml beakers with 100 ml buffer (or detergent) eas positioned in a Terg-O-Meter and equilibrated to 35° C. Then two 7×7 cm swatches of black, woven cotton cloth was added to each beaker, the stirrers were put in motion, and finally enzyme was added: A) A blank, B) Three different dosages of a standard (e.g. the commercial available enzyme preparation Celluzyme™), and C) Two different dosages of the inventive endoglucanase. Incubation then proceeded for 30 minutes at 35° C.

After the 30 minutes of incubation the swatches were rinsed in cold tap water for 10 minutes and dried in a tumble dryer.

The cycle of incubation and rinsing/drying was repeated once—or until the swatches clearly differed in respect to colour and/or fuzz in the swatches surface.

Finally the swatches were graded against the blank (no enzyme) and the standard (e.g. Celluzyme) swatches. Visual grading was performed by a panel of trained graders, and colour was measured with a remission spectrometer. Results are expressed in Table 1 as "Colour Clarification" (CC) of the swatches obtained per activity unit of enzyme.

TABLE 1

| Enzyme | Cellulase Family | CC - black, woven |
|---|---|---|
| Celluzyme | multi-component | 1.0 |
| Blank | no enzyme | 0.0 |
| Saccharothrix australiensis | endoglucanase | 1.8 |

LITERATURE

Ausubel, F. M. et al. (eds.) "Current protocols in Molecular Biology". John Wiley and Sons, 1995.

Axelsen, N., et al. in: A Manual of Quantitative Immunoelectrophoresis, Blackwell Scientific Publications, 1973, Chapter 23.

Denman, S. et al.: Characterization of a Neocallumastix patriarum cellulase cDNA (celA) homologous to Trichoderma reesei cellobiohydrolase II, Appl. Environ. Microbiol. (1996), 62(6), 1889–1896.

Damude, H. G. et al.: Substrate specificity of endoglucanase A from Cellulomonas fimi: fundamental differences between endoglucanases and exoglucanases from family 6, Biochem.J. (1996), 315(2), 467–72.

Devereux et al. (1984) Nucleic Acids Res. 12, 387–395.

Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis. J. Bacteriol.*, 172, 4315–4321

Dretzen, G., Bellard, M., Sassone-Corsi, P., Chambon, P. (1981) A reliable method for the recovery of DNA fragments from agarose and acrylamide gels. Anal. Biochem., 112, 295–298.

Feinberg, A. P. and Vogelstein, B. (1983) *Anal. Biochem.* 132:6–13.

Gilbert, H. J. and Hazlewood, G. P. (1993) J. Gen. Microbiol. 139:187–194.

Gilkes, N. R., Henrissat, B., Kilburn, D. G., Miller Jr., R. C. and Warren, R. A. J.: Domains in microbial β-1,4-glycanases; sequence conservation, function, and enzyme families. Microbiol. Rev. 55 (1991), 305–315.

Harwood, C. R., and Cutting, S. M. (eds.) "Molecular Biological Methods for Bacillus". John Wiley and Sons, 1990.

Henrissat, B.: A classification of glycosyl hydrolases based on amino acid sequence similarities. Biochem. J. 280 (1991), 309–316.

Henrissat, B., and Bairoch, A.: New families in the classification of glycosyl hydrolases based on amino acid sequence similarities. Biochem. J. 293 (1993), 781–788.

Johnstone, A. and R. Thorpe, Immunochemistry in Practice, Blackwell Scientific Publications, 1982 (pp. 27–31).

Leatherbarrow, R. J. (1992) Grafit version 3.0 Erithacus Software Ltd. Staines, U.K.

Lever, M. (1972) A new reaction for colormetric determination of carbohydrates. Anal. Biochem. 47, 273–279.

O. Ouchterlony in: Handbook of Experimental Immunology (D. M. Weir, Ed.), Blackwell Scientific Publications, 1967, pp. 655–706.

Pitcher, D. G., Saunders, N. A., Owen, R. J. (1989): Rapid extraction of bacterial genomic DNA with guanidium thiocyanate. Lett. Appl. Microbiol., 8, 151–156).

Sambrook et al. (1989) Molecular cloning: A laboratory manual, Cold Spring Harbor lab., Cold Spring Harbor, N.Y.

Quillet, L. et al.: The gene encoding the beta-1,4-endoglucanase (Cel) from Myxococcus xanthus: evidence for independent acquisition by horizontal transfer of binding and catalytic domains from actinomycetes, Gene (1995), 158(1), 23–9.

What is claimed is:

1. An endo-β-1,4-glucanase derived from a strain belonging to the genus Saccharothrix, comprising one of:
   (a) a polypeptide sequence comprising (i) a cellulose binding domain (CBD), (ii) a catalytically active domain (CAD), and (iii) a linking region encoded by a polynucleotide sequence comprising nucleotides 436–675 of SEQ ID NO:1, wherein the linking region operably linking the CBD and the CAD of the endo-β-1,4-glucanase;
   (b) a polypeptide exhibiting endo-β-1,4-glucanase activity encoded by a polynucleotide sequence which hybridizes with the polynucleotide sequence encoding the polypeptide of (a) under the conditions of hybridization at 45° C. for 12 hrs, followed by repeated washing in 2×SSC, 0.5% SDS at 55° C.–75° C., and
   (c) a polypeptide comprising the amino acid sequence of positions 20–490 of SEQ ID NO:2.

2. The endo-β-1,4-glucanase of claim 1, wherein the CBD is encoded by a polynucleotide comprising nucleotides 60–435 of SEQ ID NO:1, and the CAD is encoded by a polynucleotide sequence comprising nucleotides 676–1470 of SEQ ID NO:1.

3. The endo-β-1,4-glucanase of claim 1, wherein the strain is selected from the group of species consisting of Saccharothrix australiensis, Saccharothrix texasensis, Saccharothrix waywayandensis, Saccharothrix cryophilis, Saccharothrix flava, Saccharothrix coeruleofusca, Saccharothrix longispora, Saccharothrix mutabilis ssp. capreolus, Saccharothrix aerocolonigenes, Saccharothrix mutabilis ssp. mutabilis, Saccharothrix syringae, and Saccharothrix sp.

4. An enzyme preparation comprising the polypeptide of claim 1.

5. The preparation of claim 4, further comprising one or more enzymes selected from the group consisting of proteases, cellulases, β-glucanases, hemicellulases, lipases, peroxidases, laccases, α-amylases, glucoamylases, cutinases, pectinases, reductases, oxidases, phenoloxidases, ligninases, pullulanases, pectate lyases, xyloglucanases, xylanases, pectin acetyl estetases, polygalacturonases, rhamnogalacturonases, pectin lyases, mannanases, pectin methylesterases, cellobiohydrolases, transglutaminases; or mixtures thereof.

6. The endo-β-1,4-glucanase of claim 3, wherein the strain is selected from the group consisting of Saccharothrix australiensis, IFO 14444; Saccharothrix flava, ATCC 29533; Saccharothrix coeruleofusca, ATCC 35108; Saccharothrix longispora, ATCC 35109; Saccharothrix mutabilis ssp. capreolus, ATCC 23892; Saccharothrix aerocolonigenes, ATCC 23870; Saccharothrix mutabilis ssp. mutabilis, ATCC 31520; Saccharothrix syringae, DSM 43886; and Saccharothrix sp., IFO 13785.

* * * * *